US010568672B2

(12) United States Patent
McWilliam et al.

(10) Patent No.: US 10,568,672 B2
(45) Date of Patent: Feb. 25, 2020

(54) ANATOMIC OSTEOTOMY WEDGE

(71) Applicant: ARTHREX, INC., Naples, FL (US)

(72) Inventors: James McWilliam, Rye, NY (US); William Michael Karnes, Naples, FL (US); Karen Leigh Gallen, Naples, FL (US); Kent Ellington, Charlotte, NC (US)

(73) Assignee: ARTHREX, INC., Naples, FL (US)

( * ) Notice: Subject to any disclaimer, the term of this patent is extended or adjusted under 35 U.S.C. 154(b) by 409 days.

(21) Appl. No.: 14/515,879

(22) Filed: Oct. 16, 2014

(65) Prior Publication Data

US 2016/0106544 A1    Apr. 21, 2016

(51) Int. Cl.
*A61F 2/42*     (2006.01)
*A61B 17/80*    (2006.01)

(52) U.S. Cl.
CPC .............. *A61B 17/8095* (2013.01); *A61F 2310/00023* (2013.01)

(58) Field of Classification Search
CPC .... A61F 2002/4223; A61F 2002/30266; A61F 2002/30281; A61F 2002/30736; A61F 2002/30843; A61F 17/8095; A61F 17/80; A61F 17/8085; A61F 2002/4238; A61F 2002/4235; A61F 2002/4233; A61F 2002/4228; A61F 2/4225; A61F 2002/422; A61F 2002/4217; A61F 2002/4215; A61F 2002/4212; A61F 2002/4207; A61F 2/4202; A61F 2/42; A61F 2/28; A61F 2002/2839; A61F 2002/2835; A61F 2002/2842; A61F 2/30734; A61F 2002/30751; A61F 2002/30754; A61F 2002/30756; A61F 2002/30764

See application file for complete search history.

(56) References Cited

U.S. PATENT DOCUMENTS

| 6,143,032 | A  | * | 11/2000 | Schafer ................. A61F 2/442 606/247 |
| 6,143,033 | A  | * | 11/2000 | Paul ....................... A61F 2/28 623/16.11 |
| 6,579,318 | B2 | * | 6/2003  | Varga ..................... A61F 2/28 623/17.11 |
| 6,855,166 | B2 | * | 2/2005  | Kohrs ..................... A61F 2/446 623/17.11 |
| 7,060,096 | B1 | * | 6/2006  | Schopf .................. A61F 2/4455 623/17.11 |
| 7,137,997 | B2 | * | 11/2006 | Paul ..................... A61F 2/4455 623/17.11 |
| 7,500,991 | B2 | * | 3/2009  | Bartish, Jr. ........... A61F 2/4465 623/17.11 |

(Continued)

FOREIGN PATENT DOCUMENTS

WO    2011082343 A9    8/2011

OTHER PUBLICATIONS

Robert Anderson, MD and Thomas Lee, MD, "Biofoam Wedge System Surgical Technique", Wright Medical Technology, Inc. Copyright 2010.

*Primary Examiner* — Alvin J Stewart

(74) *Attorney, Agent, or Firm* — Carlson, Gaskey & Olds, P.C.

(57) ABSTRACT

An osteotomy wedge according to an exemplary aspect of the present disclosure includes, among other things, an asymmetrical body that includes a perimeter established by a continuous, smooth surface. Further, the perimeter includes a concave surface.

19 Claims, 4 Drawing Sheets

(56) References Cited

U.S. PATENT DOCUMENTS

| | | | |
|---|---|---|---|
| 8,784,498 B2* | 7/2014 | Scheland | A61B 17/8061 623/18.11 |
| 9,889,014 B2* | 2/2018 | Predick | A61F 2/4202 |
| 10,383,737 B2* | 8/2019 | Tyber | A61F 2/4611 |
| 2002/0165612 A1* | 11/2002 | Gerber | A61B 17/1671 623/17.11 |
| 2007/0038303 A1* | 2/2007 | Myerson | A61B 17/562 623/21.18 |
| 2007/0198016 A1* | 8/2007 | Zang | A61B 17/80 606/86 A |
| 2008/0077247 A1* | 3/2008 | Murillo | A61F 2/30771 623/17.16 |
| 2009/0138096 A1 | 5/2009 | Myerson et al. | |
| 2010/0145459 A1* | 6/2010 | McDonough | A61B 17/8033 623/17.16 |
| 2010/0249935 A1* | 9/2010 | Slivka | A61F 2/447 623/17.16 |
| 2011/0106259 A1* | 5/2011 | Lindenmann | A61F 2/4465 623/17.16 |
| 2011/0172780 A1* | 7/2011 | Scheland | A61B 17/8061 623/18.11 |
| 2012/0010472 A1* | 1/2012 | Spann | A61B 17/02 600/214 |
| 2012/0083852 A1* | 4/2012 | Milz | A61F 2/4465 606/86 A |
| 2012/0191211 A1 | 7/2012 | Drozd | |
| 2014/0257509 A1* | 9/2014 | Dacosta | A61F 2/4225 623/21.19 |
| 2015/0057665 A1* | 2/2015 | Neal | A61B 17/15 606/87 |
| 2016/0228257 A1* | 8/2016 | Predick | A61F 2/4202 |
| 2016/0263276 A1* | 9/2016 | Tyber | A61B 17/8095 |
| 2018/0008419 A1* | 1/2018 | Tyber | A61F 2/4455 |
| 2018/0228498 A1* | 8/2018 | Dacosta | A61F 2/4606 |
| 2019/0269514 A1* | 9/2019 | Sidebotham | A61B 17/8095 |
| 2019/0365542 A1* | 12/2019 | Tyber | A61L 31/14 |

* cited by examiner

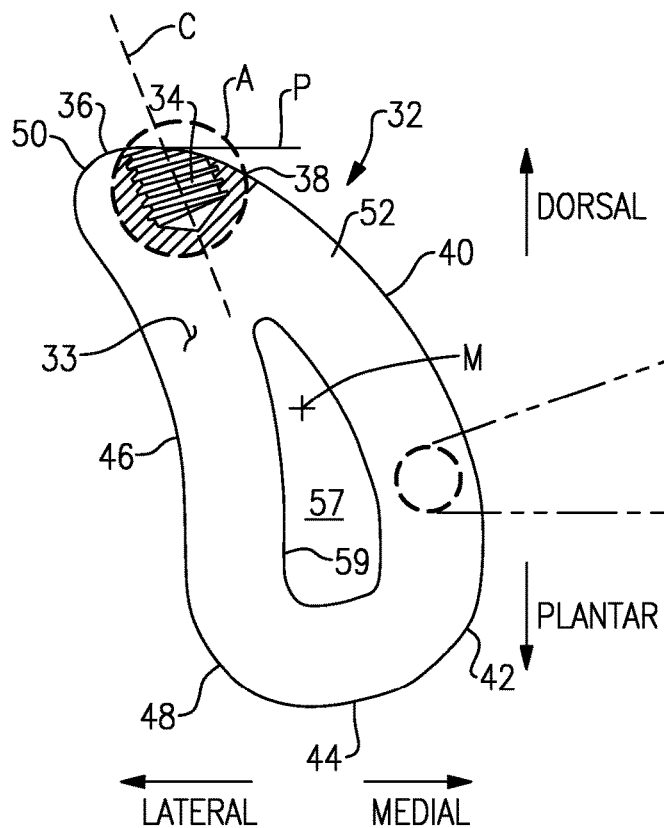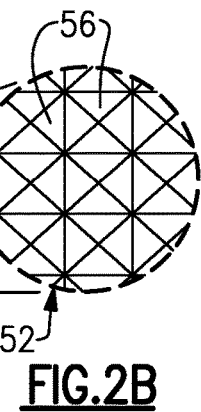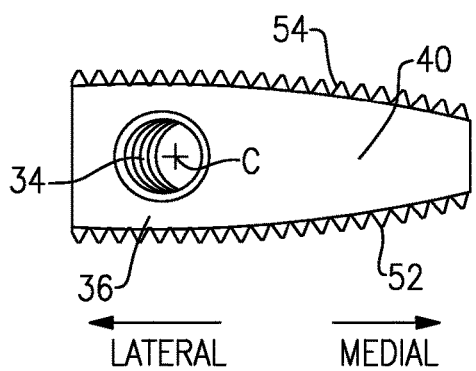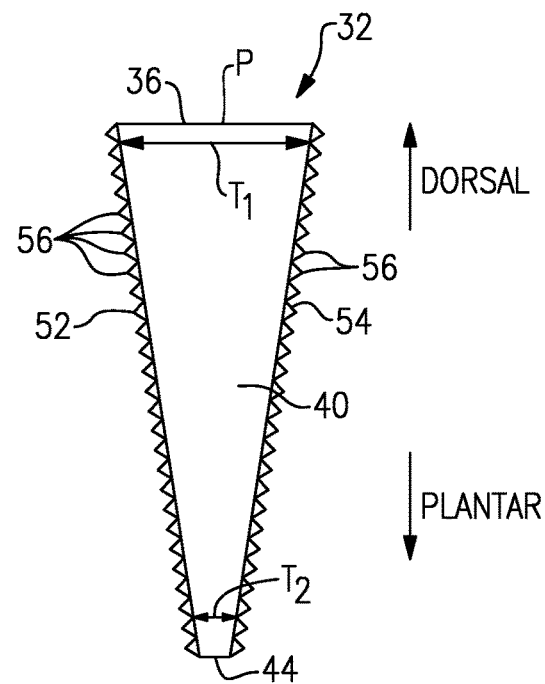

ANATOMIC OSTEOTOMY WEDGE

BACKGROUND

This disclosure relates to an anatomic osteotomy wedge and, in particular, an anatomic osteotomy wedge for a medial cuneiform bone.

An osteotomy is a surgical operation in which a bone is cut to shorten, lengthen, or change its alignment. In some osteotomies, the bone is cut and an implant is provided in the bone to change the alignment of the bone. In a medial cuneiform osteotomy, an implant is used to correct a deformity in the foot, such as flat footedness. In some medial cuneiform osteotomies, an implant with a triangular cross-section is used to align the foot. The triangular implant is symmetrical about its centerline.

SUMMARY

An osteotomy wedge according to an exemplary aspect of the present disclosure includes, among other things, an asymmetrical body that includes a perimeter established by a continuous, smooth surface. Further, the perimeter includes a concave surface.

In a further non-limiting embodiment of the foregoing osteotomy wedge, the concave surface is a plantar-lateral surface of the body.

In a further non-limiting embodiment of the foregoing osteotomy wedge, the body includes a fore surface and a hind surface, the fore surface and the hind surface each having a texture configured to engage bone.

In a further non-limiting embodiment of the foregoing osteotomy wedge, the texture includes a plurality of pyramid-shaped projections.

In a further non-limiting embodiment of the foregoing osteotomy wedge, a dorsal surface of the body provides a threaded opening.

In a further non-limiting embodiment of the foregoing osteotomy wedge, a central axis of the threaded opening is angled at a non-perpendicular angle relative to a plane provided by a dorsal surface of the body.

In a further non-limiting embodiment of the foregoing osteotomy wedge, the central axis intersects the plane.

In a further non-limiting embodiment of the foregoing osteotomy wedge, the body is made of a porous metal.

In a further non-limiting embodiment of the foregoing osteotomy wedge, the metal foam is a titanium-based porous metal.

An osteotomy wedge according to another exemplary aspect of the present disclosure includes, among other things, a body having a dorsal surface having a threaded opening. A central axis of the threaded opening is angled at a non-perpendicular angle relative to a plane provided by the dorsal surface of the body.

In a further non-limiting embodiment of the foregoing osteotomy wedge, the central axis intersects the plane.

In a further non-limiting embodiment of the foregoing osteotomy wedge, the body includes a perimeter provided by a continuous, smooth surface, the perimeter including a concave surface.

In a further non-limiting embodiment of the foregoing osteotomy wedge, the concave surface is a plantar-lateral surface of the body.

In a further non-limiting embodiment of the foregoing osteotomy wedge, the body includes a fore surface and an hind surface, the fore surface and the hind surface each having a texture configured to engage bone.

In a further non-limiting embodiment of the foregoing osteotomy wedge, the texture includes a plurality of pyramid-shaped projections.

An osteotomy wedge assembly according to an exemplary aspect of the present disclosure includes, among other things, an osteotomy wedge provided by a body, the body having a dorsal surface which provides a threaded opening. The assembly includes a fastener having a threaded shaft received in the threaded opening, and a plate secured to the osteotomy wedge by the fastener. A central axis of the threaded shaft is angled at a non-parallel angle relative to a plane provided by a surface of the plate.

In a further non-limiting embodiment of the foregoing assembly, a head of the fastener is angled at a non-perpendicular angle relative to a central axis of the threaded shaft.

In a further non-limiting embodiment of the foregoing assembly, the plate is generally rectangular and includes openings for receiving fasteners.

In a further non-limiting embodiment of the foregoing assembly, the plate includes four exaggerated corners, each of the exaggerated corners including a respective opening.

In a further non-limiting embodiment of the foregoing assembly, the plate is generally rectangular and includes two openings at each end thereof.

The embodiments, examples and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

BRIEF DESCRIPTION OF THE DRAWINGS

The drawings can be briefly described as follows:

FIG. 2A is a view of the osteotomy wedge of FIG. 1 from a forefoot direction.

FIG. 2B is a close-up view illustrating the texture of a fore surface of the osteotomy wedge of FIG. 2A.

FIG. 3 is a top view of the osteotomy wedge of FIG. 2A.

FIG. 4 is a side view of the osteotomy wedge of FIG. 2A.

DETAILED DESCRIPTION

Figure 1:
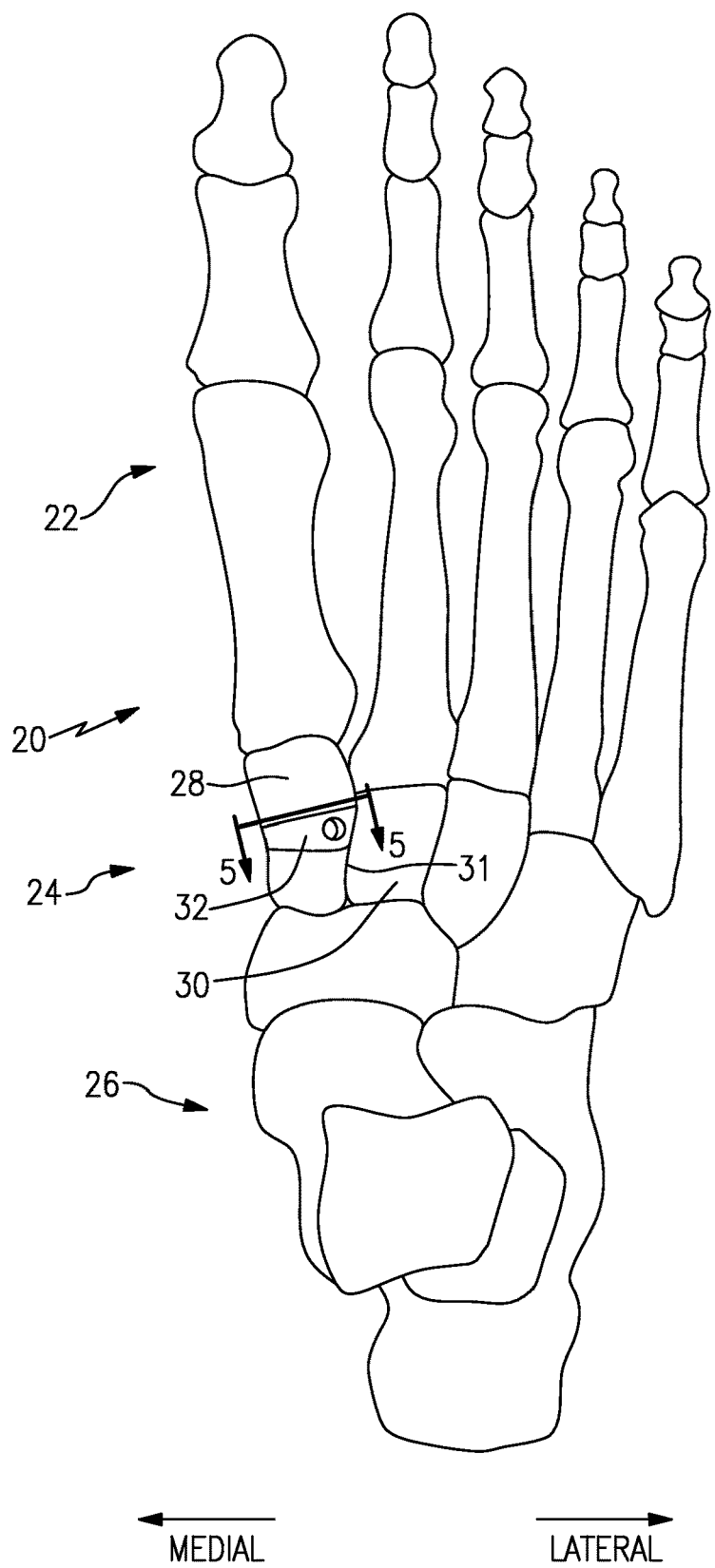
FIG. 1 is a top view of a foot including an osteotomy wedge.

FIG. 1 illustrates the bones of a foot 20 from a top (dorsal) perspective. The foot 20 includes a forefoot 22, a midfoot 24, and a hindfoot 26. The midfoot 24 includes a medial cuneiform bone 28. An inner cuneiform bone 30 is located on a lateral side of the medial cuneiform bone 28. The interface between the medial cuneiform and inner cuneiform bones 28, 30 is referred to as an intercuneiform joint 31. As illustrated, an osteotomy wedge 32 has been implanted into the medial cuneiform bone 28 to correct deformities of the foot 20. The osteotomy wedge 32 may have uses beyond the medial cuneiform bone 28.

FIG. 2A illustrates the detail of the osteotomy wedge 32 from a forefoot perspective. For purposes of illustration, FIGS. 3 and 4 show the same osteotomy wedge 32 from a top (dorsal) view and a side (medial) view, respectively.

The osteotomy wedge 32 includes a continuous, uninterrupted body 33 in this example. Further, the body 33 has an asymmetrical shape. That is, when viewed from the forefoot or hindfoot directions, it is not possible to draw an axis through a center of mass M of the body 33 such that the body 33 would be symmetrical about that axis.

FIG. 2A includes a partial sectional view at area A, which illustrates a threaded opening 34 in a dorsal surface 36 of the osteotomy wedge 32. In this example, the threaded opening 34 has a centerline C that is angled at a non-perpendicular angle (when viewed from the forefoot or hindfoot directions) relative to a plane P provided by the dorsal surface 36. This angle increases the ease of implanting the osteotomy wedge 32 into the medial cuneiform bone 28. In particular, the osteotomy wedge 32 can be more easily maneuvered when attached to an insertion instrument, such as the instrument 62 of FIG. 6.

With the exception of the threaded opening 34, the perimeter of the osteotomy wedge 32 is a continuous, uninterrupted surface. Moving clockwise from the dorsal surface 36, the perimeter of the osteotomy wedge 32 includes a first rounded corner 38, which transitions into a convex dorsomedial surface 40. The dorsomedial surface 40 transitions, via a second rounded corner 42, into a plantar surface 44, which, in turn, transitions into a plantar-lateral surface 46, via a third rounded corner 48. The plantar-lateral surface 46 is concave. Finally, the plantar-lateral surface 46 transitions, via a fourth rounded corner 50 into the dorsal surface 36.

While the outer perimeter of the osteotomy wedge 32 may be relatively smooth, fore and hind surfaces 52, 54 of the osteotomy wedge 32 may include a surface texture configured to hold the osteotomy wedge 32 in place relative to the medial cuneiform bone 28. FIG. 2B is a close-up view illustrating the texture of the fore surface 52. As illustrated in FIG. 2B, the fore surface 52 includes a plurality of pyramid-shaped projections 56 arranged in a crisscross pattern, in this example. FIGS. 3 and 4 also illustrate the projections 56. It should be understood that the hind surface 54 may include the same texture as the fore surface 52. In this example, the projections 56 are evenly distributed along the fore and hind surfaces 52, 54. While a particular surface texture is illustrated, this disclosure is not limited to any particular surface texture arrangement.

As illustrated in FIG. 4, the osteotomy wedge 32 is tapered from the dorsal surface 36 to the plantar surface 44. That is, the thickness of the osteotomy wedge 32 continuously decreases from the dorsal surface 36 to the plantar surface 44. For purposes of illustration, the osteotomy wedge 32 has a first thickness $T_1$ adjacent the dorsal surface 36, which is greater than a second thickness $T_2$ adjacent the plantar surface 44. The taper of the osteotomy wedge 32 provides the desired alignment of the medial cuneiform bone 28.

In one example, the osteotomy wedge 32 includes a central opening 57 having a contour 59 that substantially matches the contour of the perimeter of the osteotomy wedge 32. This disclosure is not limited to any particular contour for the central opening, however.

The osteotomy wedge 32 may be made of a porous metal, such as a titanium-based porous metal, in some examples. Additionally, the osteotomy wedge could be made of a PEEK (Polyether ether ketone) or a resorbable polymer material. In other examples, the osteotomy wedge includes, either in whole or in part, an allograft or xenograft. It should be understood that this disclosure is not limited to any particular material type.

Figure 5:
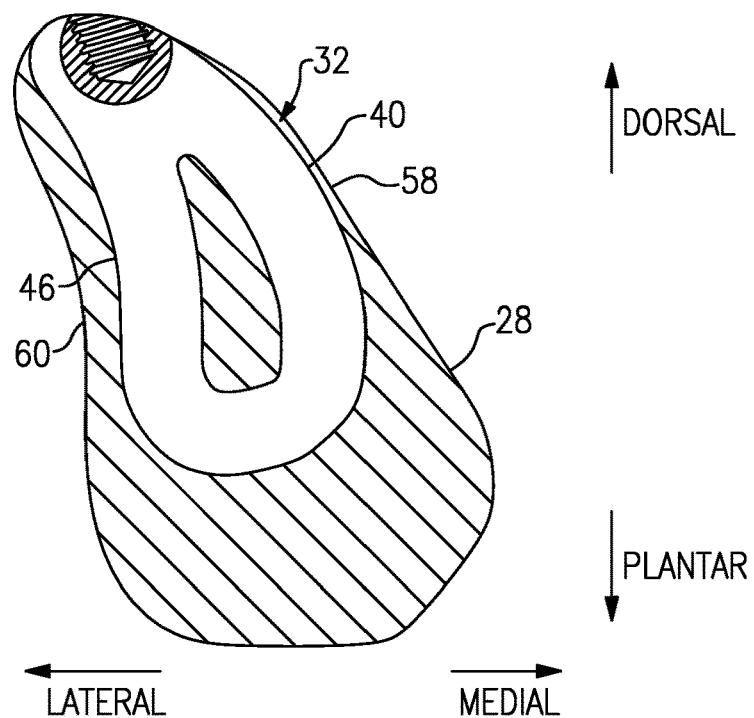
FIG. 5 is a view taken along line 5-5 from FIG. 1, and illustrates the arrangement of the osteotomy wedge relative to the medial cuneiform bone.

FIG. 5 is a sectional view taken along line 5-5 from FIG. 1 and illustrates the arrangement of the osteotomy wedge 32 relative to the medial cuneiform bone 28. As illustrated in FIG. 5, when implanted relative to the medial cuneiform bone 28, the dorsomedial surface 40 of the osteotomy wedge 32 substantially follows the contour of the dorsomedial surface 58 of the medial cuneiform bone 28. Further, the dorsomedial surface 40 of the osteotomy wedge 32 does not protrude beyond the dorsomedial surface 58 of the medial cuneiform bone 28. The convex nature of the dorsomedial surface reduces, and ideally eliminates, prominence of the dorsomedial surface 40 beyond the dorsomedial surface 58 of the medial cuneiform 28. This reduces, and ideally eliminates, contact between the osteotomy wedge 32 and the adjacent soft tissue of the foot, which may have otherwise caused irritation.

Similarly, the contour of the plantar-lateral surface 46 of the osteotomy wedge 32 substantially follows the contour of the plantar-lateral surface 60 of the medial cuneiform bone 28. Further, the plantar-lateral surface 46 of the osteotomy wedge 32 does not protrude beyond the plantar-lateral surface 60 of the medial cuneiform bone 28. The concave nature of the plantar-lateral surface 46 avoids violation of the intercuneiform joint 31, which reduces, and ideally eliminates, irritation that may have been caused by contact between the osteotomy wedge 32 and the inner cuneiform bone 30.

Figure 6:
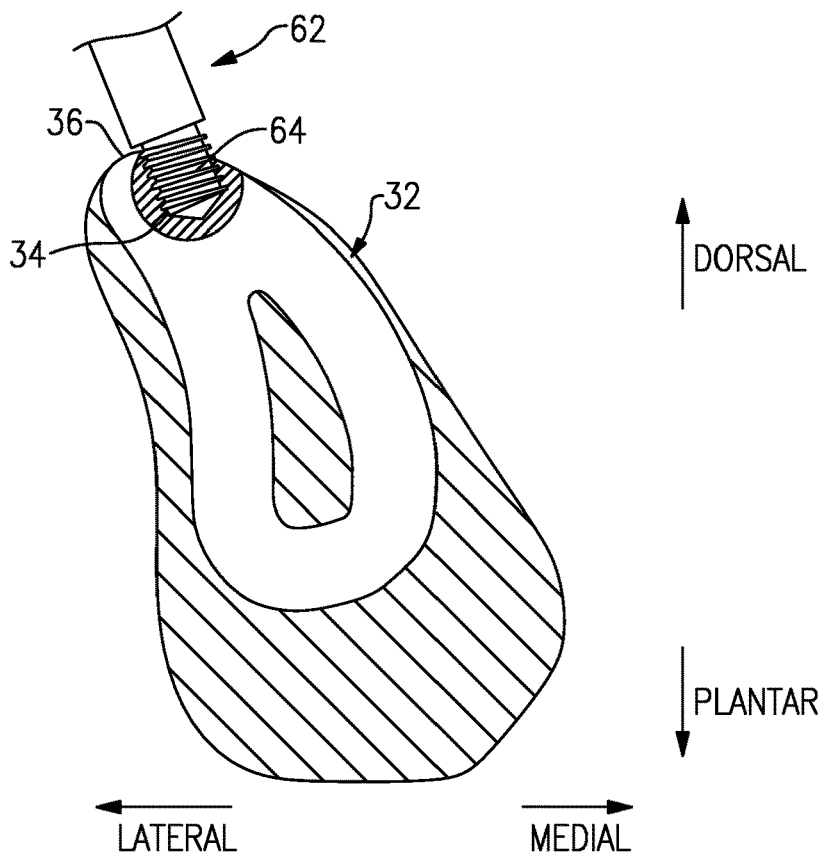
FIG. 6 illustrates an instrument used with the osteotomy wedge of FIG. 1.

FIG. 6 illustrates an instrument 62 having a threaded tip 64 at a distal end thereof for insertion into the threaded opening 34 of the osteotomy wedge 32. The instrument 62 can be used by a surgeon, for example, during surgery to insert the osteotomy wedge 32 into a cut section of the medial cuneiform bone 28. After the osteotomy wedge 32 is implanted, the instrument 62 can be unscrewed and removed from the osteotomy wedge 32. As noted above, the angle of the threaded opening 34 increases the ease of implanting the osteotomy wedge 32.

Figure 7A:
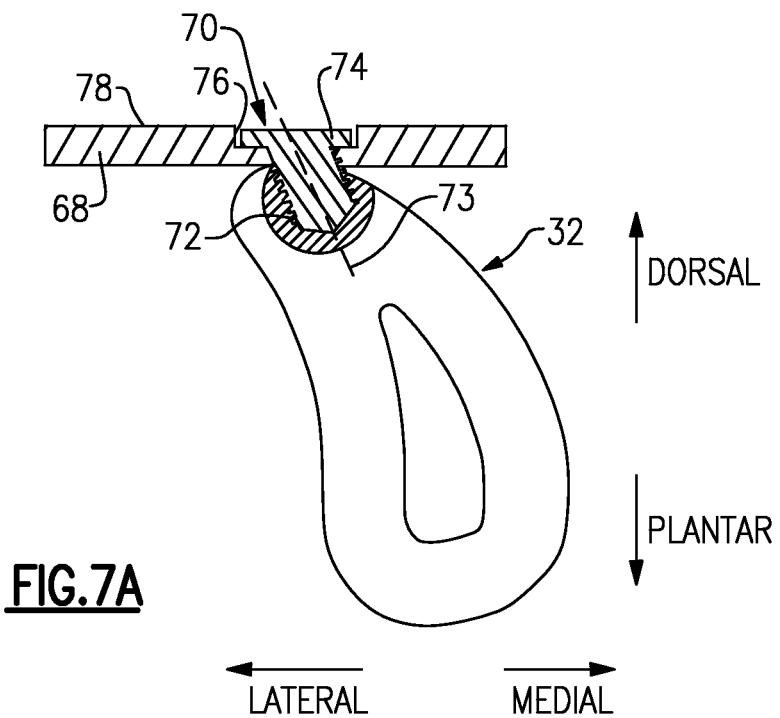
FIG. 7A illustrates an osteotomy wedge assembly including a cover plate and the osteotomy wedge of FIG. 1.

After removing the instrument 62, a plate 68 may be fastened to the osteotomy wedge 32 by way of a fastener 70. An example plate 68 and fastener 70 are illustrated in cross-section in FIG. 7A. In this example, the fastener 70 has a threaded shaft 72 that is received in the threaded opening 34. The threaded shaft 72 is arranged along an axis 73, which is angled at a non-perpendicular angle relative to both a head 74 of the fastener 70 and an upper (dorsal) surface 78 of the plate 68. In this example, the plate 68 includes a recess 76 in the upper surface 78, which is sized such that the head 74 of the screw 70 does not project beyond the upper surface 78. The recess 76 reduces irritation that the head 74 may have caused relative to the adjacent soft tissue of the foot.

Figure 7B:
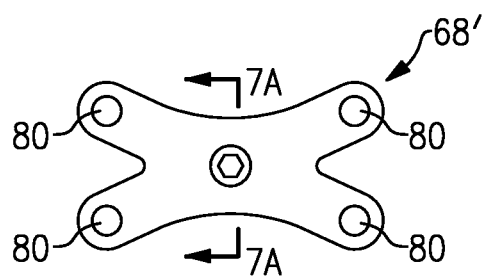
FIG. 7B is a top view of a first example cover plate.
Figure 7C:
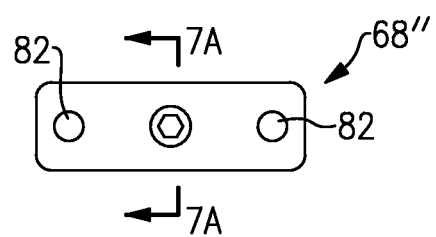
FIG. 7C is a top view of a second example cover plate.

Depending on the application, the plate 68 may be fastened to the adjacent dorsal surface of the medial cuneiform bone 28. FIG. 7B illustrates a first example configuration of the plate 68', which includes four openings 80 for receiving fasteners, such as bone screws. The plate 68' is generally rectangular with exaggerated corners. Another example plate 68" (FIG. 7C) is generally rectangular, without the exaggerated corners of the plate 68', and includes the two openings 82 for receiving fasteners. It should be understood that the plates 68' and 68" are examples only, and that this disclosure is not limited to any particular plate shape. For instance, this disclosure could be used with anatomically shaped plates.

It should be understood that while a particular osteotomy wedge shape is illustrated in the Figures, that the osteotomy wedge 32 may be scaled up or down in size in order to fit medial cuneiform bones of different sizes.

It should be understood that terms such as "fore," "hind," "dorsal," "plantar," "medial," and "lateral" are used above with reference to the normal attitude of the human body, and in this case the foot. These terms have been used herein for purposes of explanation, and should not be considered otherwise limiting. Further, terms such as "generally" and "substantially" are not intended to be boundaryless terms, and should be interpreted consistent with the way one skilled in the art would interpret the term.

Although the different examples have the specific components shown in the illustrations, embodiments of this disclosure are not limited to those particular combinations. It is possible to use some of the components or features from one of the examples in combination with features or components from another one of the examples.

One of ordinary skill in this art would understand that the above-described embodiments are exemplary and non-limiting. That is, modifications of this disclosure would come within the scope of the claims. Accordingly, the following claims should be studied to determine their true scope and content.

What is claimed is:

1. An osteotomy wedge for a foot, comprising: an asymmetrical body that includes an outer perimeter established by a continuous, smooth surface, wherein the outer perimeter includes a concave surface, wherein the body includes a fore surface, a hind surface, and a central opening extending from the fore surface to the hind surface, wherein the outer perimeter of the body is asymmetrically shaped when viewed in a direction facing one of the fore surface and the hind surface, the fore surface and the hind surface each having a texture comprising a plurality of pyramid-shaped projections arranged in a crisscross pattern, and wherein the body is tapered such that a thickness of the body continuously decreases from a dorsal surface of the body to a plantar surface of the body; and wherein the osteotomy wedge is configured to be implanted in a medial cuneiform bone to correct a deformity of the foot.

2. The osteotomy wedge as recited in claim 1, wherein the concave surface is a plantar-lateral surface of the body.

3. The osteotomy wedge as recited in claim 1, wherein the dorsal surface of the body has a threaded opening.

4. The osteotomy wedge as recited in claim 3, wherein a central axis of the threaded opening is angled at a non-perpendicular angle relative to a plane defined by a tangent to the dorsal surface of the body.

5. The osteotomy wedge as recited in claim 4, wherein the central axis intersects the plane.

6. The osteotomy wedge as recited in claim 4, wherein the plane intersects a dorsal-most point of the body.

7. The osteotomy wedge as recited in claim 1, wherein the body is made of a porous metal.

8. The osteotomy wedge as recited in claim 7, wherein the porous metal is a titanium-based porous metal.

9. The osteotomy wedge as recited in claim 1, wherein an entirety of the outer perimeter of the body is provided by a continuous, smooth surface.

10. The osteotomy wedge as recited in claim 1, wherein an outermost surface of the body establishes the outer perimeter.

11. The osteotomy wedge as recited in claim 1, wherein the body is tapered such that the thickness of the body continuously decreases from a dorsal-most point of the body to a plantar-most point of the body.

12. An osteotomy wedge for a foot, comprising: an asymmetrical body including an outer perimeter, wherein the outer perimeter of the body is asymmetrically shaped when viewed in a direction facing one of a fore surface, a hind surface of the body, and a central opening extending from the fore surface to the hind surface, and wherein the outer perimeter of the body is shaped such that the entire outer perimeter of the body is provided by a continuous, smooth surface, the body having a dorsal surface having a threaded opening, wherein a central axis of the threaded opening is angled at a non-perpendicular angle relative to a plane defined by a tangent to the dorsal surface of the body, and wherein the body is tapered such that a thickness of the body continuously decreases from the dorsal surface to a plantar surface of the body; and wherein the osteotomy wedge is configured to be implanted in a medial cuneiform bone to correct a deformity of the foot.

13. The osteotomy wedge as recited in claim 12, wherein the central axis intersects the plane.

14. The osteotomy wedge as recited in claim 12, wherein the outer perimeter includes a concave surface.

15. The osteotomy wedge as recited in claim 14, wherein the fore surface and the hind surface each have a texture configured to engage bone.

16. The osteotomy wedge as recited in claim 15, wherein the texture includes a plurality of pyramid-shaped projections.

17. The osteotomy wedge as recited in claim 16, wherein the pyramid-shaped projections are arranged in a crisscross pattern.

18. The osteotomy wedge as recited in claim 12, wherein the plane intersects a dorsal-most point of the body.

19. An osteotomy wedge, comprising:
an asymmetrical body including an outer perimeter, wherein the outer perimeter of the body is asymmetrically shaped when viewed in a direction facing one of a fore surface and a hind surface of the body, and wherein the outer perimeter of the body is shaped such that the entire outer perimeter of the body is provided by a continuous, smooth surface, the body having a dorsal surface having a threaded opening, wherein a central axis of the threaded opening is angled at a non-perpendicular angle relative to a plane defined by a tangent to the dorsal surface of the body, wherein the body is tapered such that a thickness of the body continuously decreases from the dorsal surface to a plantar surface of the body, wherein the outer perimeter includes a concave surface, and wherein the concave surface is a plantar-lateral surface of the body.

* * * * *